(12) United States Patent
Scholan

(10) Patent No.: US 11,986,265 B2
(45) Date of Patent: May 21, 2024

(54) SUPPLY LINE FOR A ROBOTIC ARM INSTRUMENT

(71) Applicant: CMR Surgical Limited, Cambridge (GB)

(72) Inventor: Andrew Murray Scholan, Waltham Cross (GB)

(73) Assignee: CMR Surgical Limited, Cambridge (GB)

( * ) Notice: Subject to any disclaimer, the term of this patent is extended or adjusted under 35 U.S.C. 154(b) by 0 days.

(21) Appl. No.: 17/201,241

(22) Filed: Mar. 15, 2021

(65) Prior Publication Data
US 2021/0196421 A1   Jul. 1, 2021

Related U.S. Application Data

(62) Division of application No. 15/558,132, filed as application No. PCT/GB2016/050702 on Mar. 15, 2016, now abandoned.

(30) Foreign Application Priority Data

Mar. 17, 2015 (GB) ..................................... 1504486

(51) Int. Cl.
*A61B 46/10* (2016.01)
*A61B 17/00* (2006.01)
(Continued)

(52) U.S. Cl.
CPC .............. *A61B 46/10* (2016.02); *A61B 34/30* (2016.02); *A61B 2017/00477* (2013.01); *A61B 2018/00595* (2013.01); *A61B 18/1206* (2013.01)

(58) Field of Classification Search
CPC ......... A61B 46/00; A61B 46/10; A61B 46/20; A61B 46/23; A61B 46/27; A61B 46/30;
(Continued)

(56) References Cited

U.S. PATENT DOCUMENTS 3,968,792 A * 7/1976 Small .................... A61B 46/27
128/851
5,122,904 A   6/1992 Fujiwara et al.
(Continued)

FOREIGN PATENT DOCUMENTS

DE   202007002332 U1   5/2004
JP   H08322851 A   12/1996
(Continued)

OTHER PUBLICATIONS

International Search Report and Written Opinion dated May 25, 2016, for International Patent Application No. PCT/GB2016/050702.
(Continued)

*Primary Examiner* — Michelle J Lee
*Assistant Examiner* — Robin Han
(74) *Attorney, Agent, or Firm* — Renner, Otto, Boisselle & Sklar, LLP

(57) ABSTRACT

A surgical robotic arm drape, the drape comprising: a sheet defining a cavity for housing a robotic arm; and a set of guiding elements attached to the sheet configured to retain a supply line threaded there through for use in a surgical procedure.

12 Claims, 11 Drawing Sheets

(51) Int. Cl.
   *A61B 18/00* (2006.01)
   *A61B 18/12* (2006.01)
   *A61B 34/30* (2016.01)

(58) Field of Classification Search
   CPC ......... A61B 46/40; A61B 34/30; A61B 90/25; A61B 2046/234; A61B 2046/236; A61B 2018/00595; A61B 2017/00477; A61B 18/1206
   USPC ............... 128/852; 206/316.1; 74/490.02
   See application file for complete search history.

(56) References Cited

U.S. PATENT DOCUMENTS

| | | | |
|---|---|---|---|
| 7,096,870 | B2 | 8/2006 | Lamprich et al. |
| 9,127,786 | B1 | 9/2015 | Arratia |
| 10,213,267 | B2 | 2/2019 | King et al. |
| 2006/0191540 | A1 | 8/2006 | Lamprich et al. |
| 2007/0107130 | A1 | 5/2007 | Elhabashy |
| 2010/0030233 | A1* | 2/2010 | Whitman ............... A61B 34/30 606/130 |
| 2011/0088702 | A1* | 4/2011 | King ..................... A61B 46/10 128/852 |
| 2012/0065472 | A1 | 3/2012 | Doyle et al. |
| 2013/0269713 | A1 | 10/2013 | Bui et al. |
| 2014/0318551 | A1 | 10/2014 | Daly |
| 2015/0090063 | A1* | 4/2015 | Lantermann ......... B25J 19/0025 74/490.02 |

FOREIGN PATENT DOCUMENTS

| | | |
|---|---|---|
| JP | 2008514354 A | 5/2008 |
| JP | 2014076204 | 5/2014 |
| WO | 2006038948 | 4/2006 |
| WO | 2013160239 | 10/2013 |
| WO | 2014109706 | 7/2014 |

OTHER PUBLICATIONS

Search Report dated Aug. 28, 2015, for GB Patent Application No. GB1504486.0.
Office Action dated Jul. 8, 2020, for corresponding European Patent Application No. 16712400.7.
Notice of Reasons for Refusal dated Sep. 4, 2020, for corresponding Japanese Patent Application No. 2017-548961.
3rd Notification of Office Action dated Feb. 25, 2021, for corresponding Chinese Patent Application No. 201680016136.9.

* cited by examiner

SUPPLY LINE FOR A ROBOTIC ARM INSTRUMENT

BACKGROUND

This invention relates to securing a supply line for servicing a surgical robotic instrument to a surgical robotic drape. More particularly, aspects relate to a drape having a supply line interposed between interior and exterior surfaces of a drape sheet and to a drape having a set of guiding elements attached to the drape sheet to retain a supply line threaded through the guiding elements.

FIG. 1 shows a typical surgical robot for performing robotic surgery. The surgical robot 101 comprises a robotic arm 103 attached at one of its ends to a surgical instrument 105. The surgical instrument is operable to pass into a patient for performing surgery. The robotic arm comprises one or more joints 107 about which the arm can be articulated to control the movement and/or position of the surgical instrument. The robotic arm 103 is shrouded by a surgical drape 109 to provide a sterile boundary between the surgical instrument (which must be sterile) and the robotic arm (which may not be sterile). The drape provides a boundary between the robotic arm and the sterile field in which the arm is positioned (for example an operating theatre).

The robotic instrument may be serviced by one or more supply lines. For example, the surgical instrument 105 may be electrically powered to enable the instrument to perform surgical operations such as cauterisation or cutting. In such cases the supply line may be a power cable 111 for supplying power to the surgical instrument. The power cable may connect to an external power supply such as a generator 113 for supplying power to the surgical instrument. One approach for arranging the supply lines in a surgical procedure is to string the supply lines along the exterior surface of the drape to reduce the risk of the supply line being a safety hazard. The supply line may be attached to the drape using tape, cable ties or other similar components. One drawback with this approach is that it may be awkward to attach the supply line to the drape, particularly under sterile conditions, potentially contributing to the difficulty in preparing a surgical robot for a procedure.

There is therefore a need for an improved way to attach a supply line to a robotic arm drape.

SUMMARY

According to one aspect of the present disclosure there is provided a surgical robotic arm drape for enveloping a portion of a robotic arm, the drape comprising: a sheet configured to define a cavity for housing a portion of a robotic arm, the sheet comprising an interior surface and an exterior surface; and a power cable interposed between the interior and exterior surfaces of the sheet for supplying power to a robotic arm instrument.

The power cable may be sandwiched between the interior and exterior surfaces of the sheet.

The power cable may be housed within a channel defined by material of the sheet, the channel being interposed between the interior and exterior surfaces of the sheet.

The power cable may comprise a conductive core, the core being surrounded by an insulating sheath.

The sheath may be formed from material of the sheet.

The material of the sheet may interface directly with the conductive core.

The power cable may comprise a conductive core and an insulating sheath that surrounds the conductive core.

The sheath may be formed from material which is not integral with the material of the sheet.

The power cable may terminate at a first of its ends in a supply connector configured to connect to a power supply, and at a second of its ends in an instrument connector configured to connect to a robotic arm instrument.

The power cable may traverse the exterior surface of the sheet proximal to the instrument connector.

The power cable may be configured to not traverse the interior surface of the sheet.

The drape may be configured so that the sheet defines an elongate cavity and the power cable extends along a longitudinal extent of the cavity.

The power cable may extend between an opening mouth of the cavity for housing a basal portion of the robotic arm instrument and a distal end of the cavity for housing a distal portion of the robotic arm instrument.

At least one of the supply connector and the instrument connector may be exterior to the cavity defined by the sheet.

The power cable may comprise a solid core.

The conductive core may comprise a plurality of conductive strands in a braided or twisted arrangement.

According to a second aspect of the present disclosure there is provided a surgical robotic arm drape for enveloping a portion of a robotic arm, the drape comprising: a sheet configured to define a cavity for housing a portion of a robotic arm, the sheet comprising an interior surface and an exterior surface; and a supply line interposed between the interior and exterior surfaces of the sheet for use in a surgical procedure.

According to a third aspect of the present disclosure there is provided a surgical robotic arm drape, the drape comprising: a sheet defining a cavity for housing a robotic arm; and a set of guiding elements attached to the sheet configured to retain a supply line threaded therethrough for use in a surgical procedure.

The set of guiding elements may be spatially arranged on the sheet so that a supply line threaded therethrough is positioned for use in the surgical procedure when the drape houses the robotic arm.

Each of the guiding elements in the set may define a loop of material for receiving the threaded supply line.

Each of the guiding elements in the set may define a conduit portion for receiving the threaded supply line.

Each of the guiding elements may comprise a housing defining a channel for receiving the threaded supply line.

Each of the guiding elements may be configured to receive a plurality of supply lines.

The drape may further comprise a second set of guiding elements for retaining a second supply line for use in a surgical procedure.

The drape may further comprise a supply line threaded through the set of guiding elements.

According to a fourth aspect of the present disclosure there is provided a surgical robotic system, comprising: a surgical robotic arm having a surgical instrument attached thereto; a surgical robotic arm drape comprising a sheet defining a cavity that houses the robotic arm, and a set of guiding elements attached to the sheet to retain a robotic-instrument supply line; and a supply line threaded through the set of guiding elements for use in a surgical procedure.

The set of guiding elements may be spatially arranged on the sheet so that the supply line is positioned to service the surgical instrument.

The supply line may be a power cable for supplying power to the surgical instrument.

The power cable may comprise a first terminal end for connecting to a power supply and a second terminal end for connecting to the surgical instrument, and the set of guiding elements are spatially arranged on the sheet so that the second terminal end of the power cable is positioned for connection to the surgical instrument.

The set of guiding elements may be positioned on the sheet so as to extend along the longitudinal extent of the cavity. The set of guiding elements may be positioned on the sheet so as to extend along the direction of the robotic arm.

Each of the guiding elements in the set may define a loop of material through which the supply line is threaded.

Each of the guiding elements in the set may define a conduit portion through which the supply line is threaded.

The system may comprise a plurality of supply lines, each threaded through the set of guiding elements.

The drape may further comprise a second set of guiding elements attached to the sheet; and a second supply line threaded through the second set of guiding elements for use in a surgical procedure.

The set of guiding elements may be integral with the sheet.

The set of guiding elements may be detachable from the sheet.

The set of guiding elements may be attached to an exterior surface of the sheet.

The set of guiding elements may be attached to an interior surface of the sheet, and the sheet may comprise a sealable opening located at a distal end of the cavity through which a terminal end of the supply line can pass.

The guiding elements may be arranged to permit relative motion of the supply line and sheet. Each of the guiding elements may be rotatably connected to the sheet.

The supply line could be one of: a power cable for supplying power to a surgical instrument, an irrigation tube, a suction tube or a data cable.

The drape forming part of the system may be any of the drapes according to the first second and third aspects of the present disclosure.

According to another aspect of the present disclosure there is provided a surgical robotic arm drape comprising: a sheet defining a cavity for housing a robotic arm; a set of guiding elements attached to the sheet configured to retain a supply line threaded therethrough for use in a surgical procedure; and a supply line threaded through the set of guiding elements. The drape may additionally comprise any of the features of the drape of the second, third and fourth aspects of the disclosure.

BRIEF DESCRIPTION OF DRAWINGS

The present invention will now be described by way of example with reference to the accompanying drawings. In the drawings.

Where appropriate, like reference numerals have been used in the following description to refer to like features, or components.

DETAILED DESCRIPTION

Figure 1:
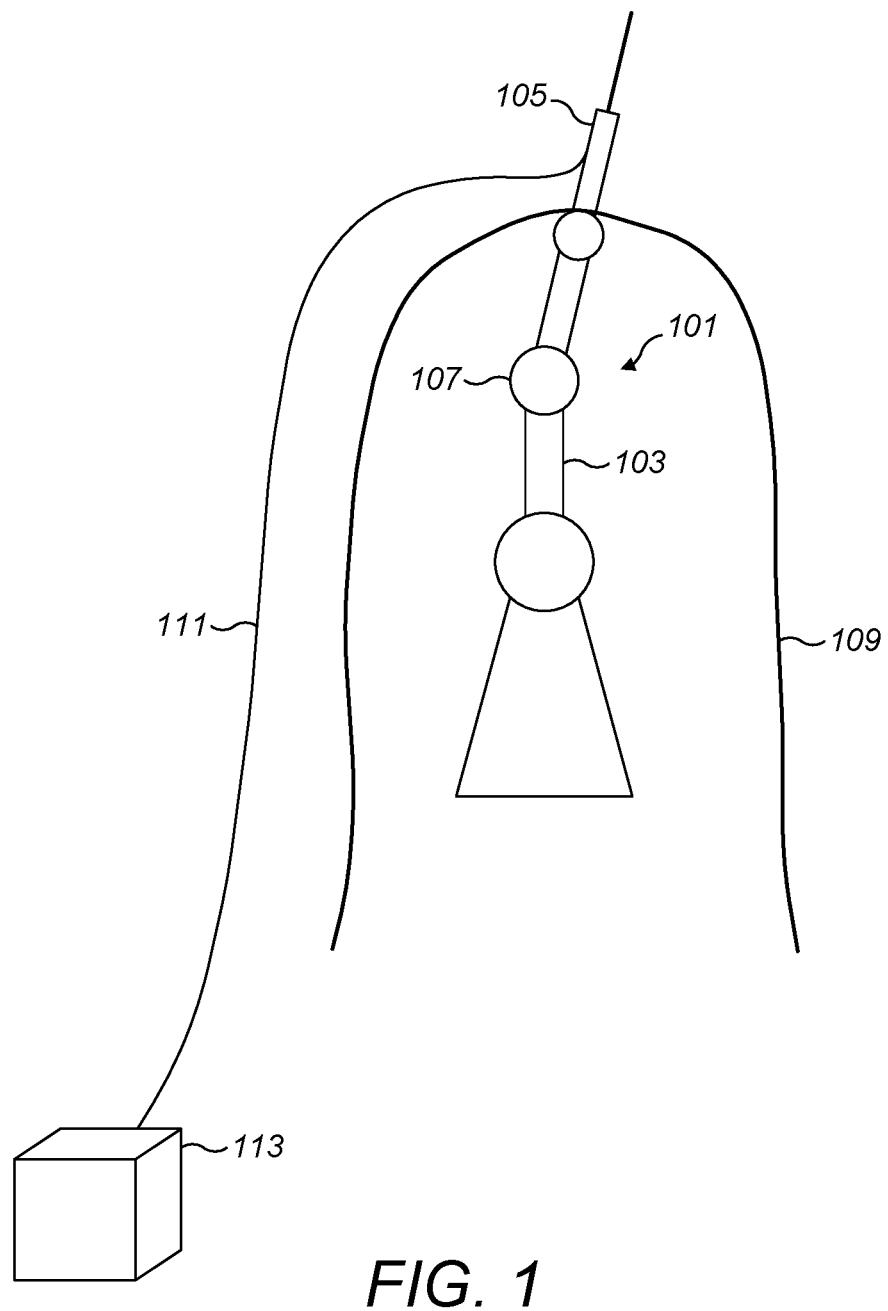
FIG. 1 shows a typical set-up of a surgical robot for performing a surgical procedure.

A surgical robotic arm drape is used to envelope a portion of a robotic arm, for example during a surgical procedure. The surgical drape comprises a sheet that defines a cavity for housing at least a portion of the robotic arm. The robotic arm may have attached thereto a surgical instrument for performing a surgical procedure on a patient. The drape may be fitted to shroud the robotic arm but to leave the instrument uncovered. In this manner the drape defines a sterile barrier around the robotic arm (which may not be sterile) whilst leaving the instrument (which is sterile) free to perform the surgical procedure. The drape sheet comprises an interior surface that interfaces with the non-sterile environment surrounding the robotic arm, and an exterior surface that interfaces with the sterile environment.

During a surgical procedure, one or more supply lines may be used to service the robotic instrument or assist the surgeon in performing the surgical procedure. The supply lines may connect to the instrument, for example by attaching to an interface located on the instrument. They may alternatively connect to the robotic arm. The supply lines may service the instrument by enabling the instrument to perform one or more of its functions, or by providing one or more services to the instrument during a surgical procedure. The supply line could for example be a power cable for supplying power to the instrument (e.g. if the instrument was electrically powered). Alternatively, the supply line may be a tube or conduit for maintaining the condition of a surgical site during a procedure, for example by removing fluid and/or debris from the surgical site; that is the supply line may be a suction tube or irrigation tube. In another example, the supply line could be a data transmission cable for communicating data and/or control signals to and/or from the surgical instrument or robotic arm. The control signals could for example be signals transmitted from the surgeon's input controls. In a further example, the supply line could be an optical fibre, or an endoscope. In general, the supply line could be a cable, or lead (e.g. a data transmission cable or power supply cable), or a tube (e.g. an irrigation tube or suction tube). The supply line may also be referred to as a conduit.

Described herein are various examples of securing a supply line/conduit to the drape sheet that may expedite set-up of the surgical robot by eliminating the need to manually string the supply line/conduit along the sheet using ties, tape etc. In a first set of examples described with reference to FIGS. 2 to 8, the supply line is interposed between the interior and exterior surfaces of the drape sheet. In a second set of examples described with reference to FIGS. 9 to 11, the supply line is secured to the surgical sheet via a set of guiding elements that retain the supply line.

The first set of examples will now be described. In these examples, the supply line is a power cable for supplying electrical power to the surgical instrument. It will be appreciated that this is for the purpose of illustration only, and the following description is equally applicable for any of the various forms of the supply line. In these examples the cable is between the interior and exterior surfaces of the sheet. The cable may be housed within a conduit defined by material of the sheet. Making the power cable integral with the drape sheet negates the need to manually set up and secure the power cable to the drape during set-up of the surgical robot. This may make the set-up of the robot for a surgical procedure easier and quicker compared to the situation in which the power cable is a separate and distinct component that requires manual securement to the drape.

Figure 2:
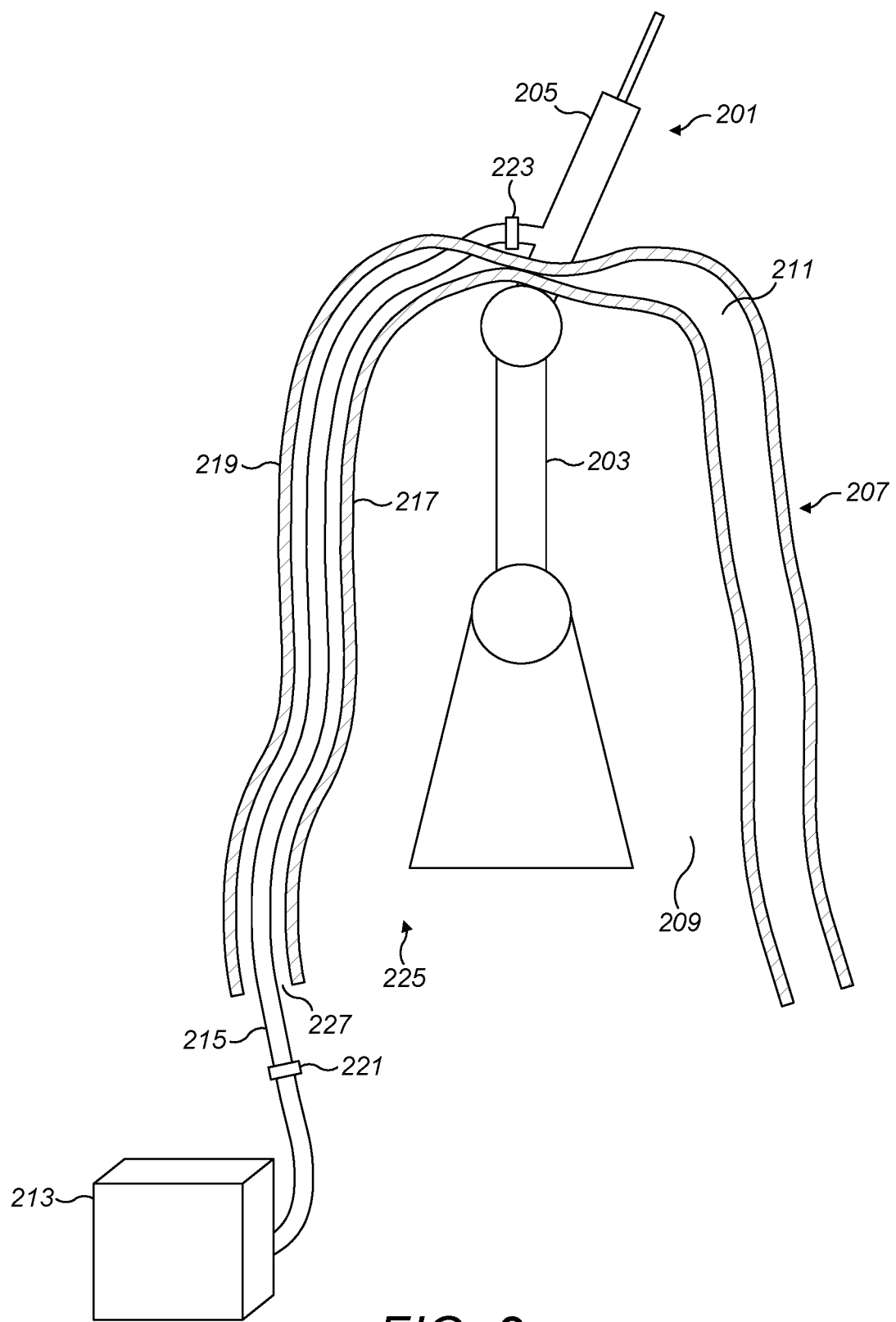
FIG. 2 shows a cross-sectional view of a surgical drape enveloping a portion of a robotic arm with a power cable interposed between interior and exterior surfaces of the drape sheet.

FIG. 2 shows an example of a surgical robot set up to perform a surgical procedure. The surgical robot is indicated generally at 201 and comprises a robotic arm 203 and a surgical instrument 205. A surgical drape 207 envelopes the robotic arm to define a sterile boundary thereover. The drape is shown in cross-sectional view (indicated by the hatched markings). The drape comprises a sheet 211 that defines a cavity 209 that houses the robotic arm. The sheet comprises an interior surface 217 and an exterior surface 219. The interior surface interfaces with the cavity 209 and the exterior surface interfaces with the external environment. When the surgical robot is set up to perform a surgical procedure, the interior surface may interface with the non-sterile environment and the exterior surface may interface with the sterile environment.

The sheet 207 may be flexible so as to permit a degree of compliance in the drape to make it suitable for use with a range of robotic arms of differing sizes and shapes. The sheet may be made of material such as polyester, polypropylene, polyethylene or polytetrafluoroethylene (PTFE) for example.

The surgical instrument 205 is powered by an external power supply (shown here as a generator 213). Power is supplied from the power supply 213 to the instrument 205 via a power cable 215. The power cable is interposed between the interior and exterior surfaces of the drape sheet. The power cable can therefore be viewed as being embedded within the sheet. The cable may be integrated with the sheet during the manufacturing process of the drape. The power cable may be permanently embedded within the sheet. Alternatively the power cable may not be permanently embedded within the sheet but may be detachable from the sheet. The power cable may for example be integrated with the drape sheet at a time after manufacture of the sheet, e.g. in an operating theatre when the robotic instrument is being set up to perform a surgical procedure. The power cable may be integrated with the sheet by feeding the cable through an integrated conduit of the sheet. When the surgical procedure has finished, the cable may be detached from the sheet by removing the cable from the conduit.

As discussed in more detail below, the power cable may be sandwiched between the interior and exterior surfaces of the sheet so that the material of the sheet is flush with the outer surface of the cable. Alternatively the power cable may be housed within a conduit defined by the sheet material that is not flush with the surface of the cable.

The power cable may terminate at each of its ends with a connector. The power cable may comprise a supply connector 221 at one of its ends for connecting to the power supply 213, and an instrument connector 223 at the other one of its ends for connecting to the robotic arm instrument 205. The instrument connector and supply connector may be moulded connectors, for example.

The power cable need not necessarily be interposed between the interior and exterior surfaces of the sheet along its entire length. For example, the connectors may be positioned externally of the sheet 207 to facilitate connection of the cable to the instrument and/or power supply. The power cable may nevertheless be interposed between the surfaces of the sheet along a substantial part of its length so as to minimise exposure of the cable to the sterile environment. The power cable may traverse the exterior surface of the sheet (as shown) to connect to the robotic arm instrument, but not traverse the interior surface of the sheet. This is advantageous because it means the cable can be integrated within the drape without requiring a fluid passage between the non-sterile environment within the cavity to the sterile environment external to the cavity. The power cable may traverse the exterior surface of the sheet at a region proximal to the instrument connector so that the majority of the cable is interposed between the sheet surfaces.

The power cable may extend through an opening, or mouth, 227 at the perimeter of the sheet to connect to the power supply. The mouth may have a boundary, or lip, defined by the interior and exterior surfaces of the sheet, as shown. The mouth may be directed or oriented in a direction substantially parallel with the surfaces of the sheet. That is, the plane of the opening may be substantially transverse, or perpendicular to the surfaces of the sheet. Alternatively the power cable may traverse the interior surface of the sheet in a region proximal to the power connector. Typically, the power supply 213 will not be sterile. As such, it may be desirable to store the power supply in a non-sterile region and not in the sterile environment. The drape may be configured so that the power cable traverses the interior surface of the sheet to enable the power cable to connect to a power supply that is stored in a non-sterile region when the surgical robot is set up for a procedure. This is advantageous because it enables the power cable to connect to the power supply without having to store the power supply in the sterile environment. The drape may comprise a port, or opening, positioned on the interior surface of the sheet through which the cable can pass to traverse the interior surface of the sheet.

To prepare the robot 201 for a surgical procedure, the drape 207 is passed over the robotic arm 203. The drape may be manufactured in a general elongate shape that can be passed over the arm. For example the drape may be manufactured so as to have a general tubular shape, closed at one end and open at its other end. Alternatively the drape may be manufactured as a planar sheet that is manipulated into an elongate shape as the drape is fitted over the robotic arm. Regardless, the drape sheet is configured to define a cavity for housing the robotic arm. The cavity may comprise a basal end for housing a basal portion of the robotic arm, and a distal end for housing a distal portion of the robotic arm. The cavity comprises an opening, or mouth (indicated generally at 225), at its proximal or basal end that may permit the drape to be passed over the robotic arm. The mouth may be sealed against the arm to enclose a volume between the interior surface of the sheet and the exterior of the arm. The drape may be configured so that the power cable extends along a longitudinal extent of the cavity. The cable may extend from a region proximal to the basal end of the cavity to a region proximal to the distal end of the cavity. Once the drape has been passed over the robotic arm, the power cable can be connected to the instrument 205 near the distal end of the cavity, and to the power supply 213 near the opening mouth 225 of the cavity.

When preparing a surgical robot for a procedure using a conventional drape, there is typically a requirement to consider where to place the power cable so as to minimise the likelihood that it will interfere with or distract the personnel taking part in the procedure. One solution is to secure the cable to the exterior surface of the drape, however this may be an awkward and time consuming task. In addition, the power cable may need to be connected and subsequently removed each time the robot is prepared for a procedure. By interposing the cable between interior and exterior surfaces of the drape sheet, these problems may be circumvented. Because the power cable is integral with the drape sheet 207, there is no need to consider where to position and/or attach the power cable during set-up of the surgical robot. Furthermore, because the cable is sealed within the sheet, it may not require pre-sterilisation prior to use of the drape.

Figure 3:
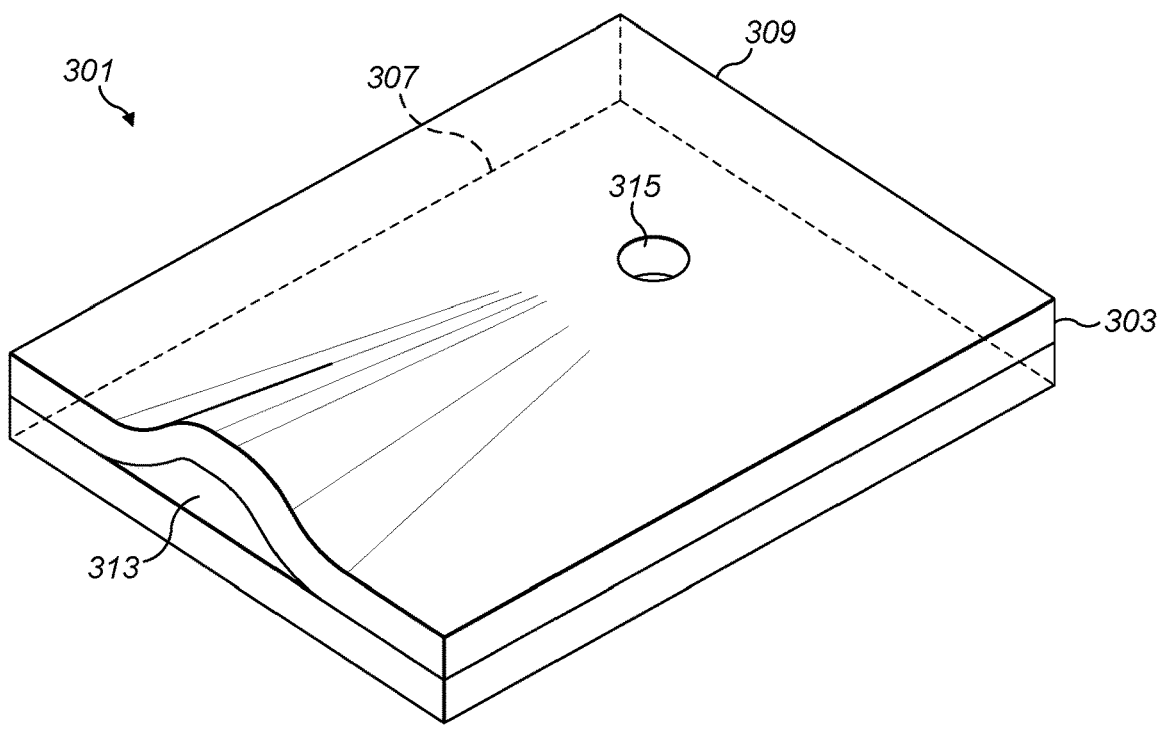
FIG. 3 shows an example of a drape in a planar arrangement.

FIG. 3 is an example of a drape shown in a planar arrangement. The drape may be constructed as a planar sheet before being fitted over a robotic arm to define a cavity that houses the arm. The drape 301 comprises a sheet 303 having an interior surface 307 and an exterior surface 309. The drape 301 comprises a duct, or channel, or conduit 311 interposed between the interior and exterior surfaces 307 and 309 respectively for housing the power cable 305. The channel extends in a direction substantially parallel to the surfaces of the sheet and has a mouth 313 located at the perimeter of the drape. The mouth may comprise an opening, and a lip formed from material of the sheet. The channel is bounded along its length by the material of the sheet. The channel is thus defined by the material of the sheet. The drape further comprises a port 315 to permit the power cable to traverse the exterior surface 309 to connect to a robotic arm instrument. The port 315 is positioned on the exterior surface. The port 315 enables the cable to extend from the channel through the exterior surface.

The drape may be manufactured without a power cable. That is, the power cable may not be embedded within the drape sheet during manufacture of the drape. A power cable can be integrated with the drape by threading the cable through the channel 311 via the mouth 313 and port 315. This may be done by a user of the drape (e.g. a surgeon or nurse). The power cable may be removed from within the sheet in a similar way. The power cable may thus be detachable from the sheet and not permanently embedded therein.

The power cable (e.g. a cable embedded in the sheet during manufacture or an integrated cable detachable from the sheet) may extend at least between the mouth of the channel and the port so that the length of cable therebetween is embedded within the sheet 303. A distal portion of the power cable may extend beyond the port 315 for connecting to the robotic instrument. This portion may comprise the instrument connector. Likewise, a proximal, or basal portion of the power cable may extend beyond the channel mouth for connecting to the external power supply. This proximal portion may comprise the supply connector.

The drape may be configured so that the channel mouth circumscribes the outer surface of the cable. In other words, the mouth may touch or be in contact with the outer surface of the cable. The mouth may be sealed against the outer surface of the cable. The channel mouth may be adhered to the surface of the cable, for example. Circumscribing the mouth around the cable may limit non-sterile air being drawn through the channel where it could potentially enter the sterile environment during a surgical procedure. Circumscribing the mouth around the cable may also help to secure the cable relative to the sheet to prevent unwanted movement of the cable. For similar reasons, the drape may also be configured so that the port likewise circumscribes the power cable.

The drape may comprise a further port or opening (not shown) in a region proximal to the perimeter of the sheet. The port may be positioned on the interior surface of the sheet to enable the cable to traverse the interior surface to connect to a power supply. This would enable the power cable to extend from the channel into a non-sterile region to connect to the power supply, as discussed above. The drape may comprise the additional port instead of the mouth 313. Alternatively the drape may comprise a port and the mouth.

Figure 4:
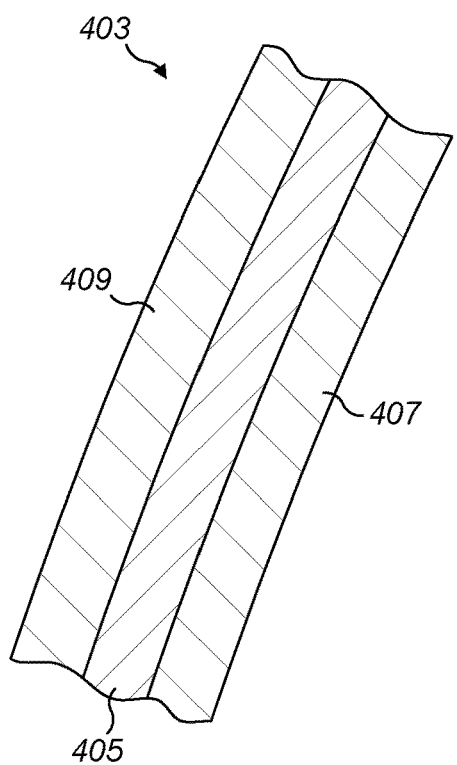
FIG. 4 shows a cross-sectional view of a drape in which a power cable is sandwiched between interior and exterior surfaces of the drape sheet.

The cable may be sandwiched between the interior and exterior surfaces of the sheet. For example the cable may sit within a channel or conduit that circumscribes the outer surface of the power cable along its length so that the material of the sheet is flush with the outer surface of the cable. The material of the sheet may touch, or be in contact with the outer surface of the cable. FIG. 4 shows an exemplary cross-section through part of a drape in which the power cable is sandwiched between interior and exterior surfaces of the sheet. The drape could for example be the drape illustrated in FIG. 2 or 3. In FIG. 4 a power cable 405 is shown housed within a channel. The power cable 405 is interposed between the interior surface 407 and the exterior surface 409 of sheet 403, and is sandwiched by those surfaces so that that the outer surface of the cable is flush with, or adhered to, the sheet material. The power cable can be said to be surrounded, or embedded, by the sheet.

The power cable may be sandwiched between the interior and exterior surfaces of the sheet during the manufacture of the drape. As such, the power cable may be permanently embedded within the sheet. An example of how the cable may be sandwiched between the surfaces of the drape sheet is described with reference to FIG. 5. As a first step, the power cable 505 may be placed on a first sheet of material 501. A second sheet of material 503 can then be placed congruently with the first sheet and the first and second sheets subsequently bonded together, for example by heat, through use of an adhesive, or a combination thereof. The outer surfaces of the two sheets of material (i.e. the surfaces of the sheets that do not interface with each other) correspond to the interior and exterior surfaces of the drape sheet 403 once the sheets are bonded together.

Sandwiching the cable between the interior and exterior surfaces of the sheet may prevent the cable from becoming dislodged during use of the drape. In addition, sandwiching the cable does not require the use of elaborate or expensive manufacturing techniques.

Figure 6:
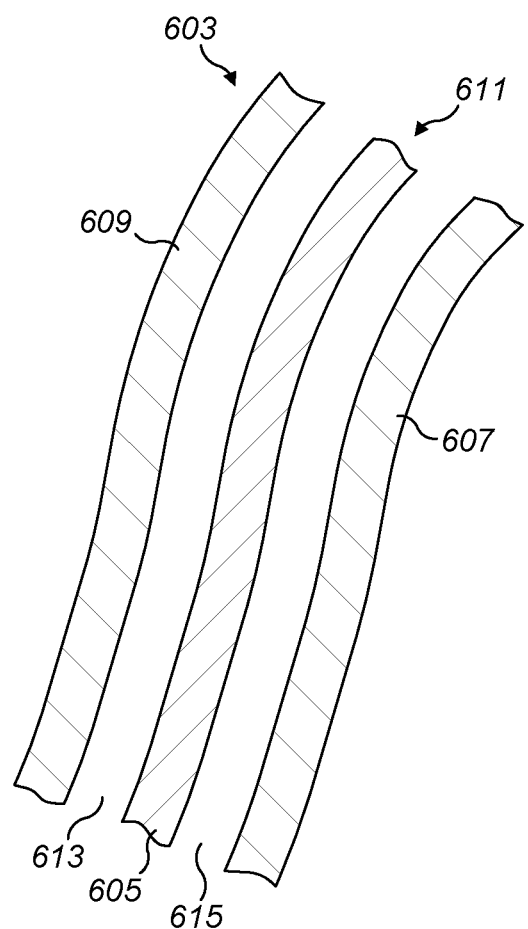
FIG. 6 shows a cross-sectional view of a drape in which a power cable is interposed between interior and exterior surfaces of the drape so that there exists an air gap between the material of the drape sheet and the outer surface of the cable

FIG. 6 shows an alternate cross-section through part of a drape. The drape could for example be the drape in FIG. 2 or 3. In this example a power cable 605 is housed within a channel or conduit 611 interposed between interior 605 and exterior 607 surfaces of a drape sheet 603, but is not circumscribed thereby. For example the drape may be configured to permit lateral movement of the power cable within the conduit. There may exist air gaps 613 and 615 between the sheet material defining the conduit and the outer surface of the power cable. The conduit may have a larger cross sectional area than the cross-sectional area of the cable. The additional space within the conduit may reduce the constraints placed by the sheet on the compliance of the power cable. This may be useful when securing the drape to the surgical robot in advance of a procedure. For example, when securing the drape to the robotic arm, the drape is manipulated through a range of structural shapes and forms. Such manipulation requires a degree of compliance from the power cable. That compliance may be increased by reducing the locomotive constraints on the cable.

A surgical drape that permits movement of the power cable within the conduit may nevertheless be configured so that the sheet material circumscribes the cable at the mouth of the conduit and/or at the port(s). This may be to secure the cable relative to the sheet and/or limit the flow of non-sterile air through the conduit. The drape may be configured so that the mouth and/or port(s) are sealed to the power cable. The sheet material could be adhered to the power cable at these locations, for example.

A drape with a cross-section as shown in FIG. 6 may be manufactured in a similar manner to the process described with reference to FIG. 5. The process would differ in that, rather than adhering together the entire surfaces of the two sheets of material 501 and 502, each sheet would be adhered to the other along two contact strips on opposing sides of the cable. The interspace between the contact strips would determine the size of the conduit relative to the size of the cable. The sheet material may then be closed off around the mouth of the conduit and/or port to seal the material in these regions to the power cable. It will be appreciated that this process is just an example and that the drape may be manufactured in other suitable ways. For example the drape may be manufactured without embedding a power cable and/or manufactured so that the power cable is detachable from the drape sheet.

The drape sheet may comprise two layers or sub-sheets of material. The two layers may be congruent. That is, the sheet may comprise two layers of material across the whole surface of the sheet. An example of such a sheet is shown in FIGS. 2, 3 and 5. The drape may alternatively be configured so that the drape sheet comprises two layers or sub-sheets only in the proximity, or surrounding area, of the power cable. An example of such a drape is shown in FIG. 7.

Figure 7:
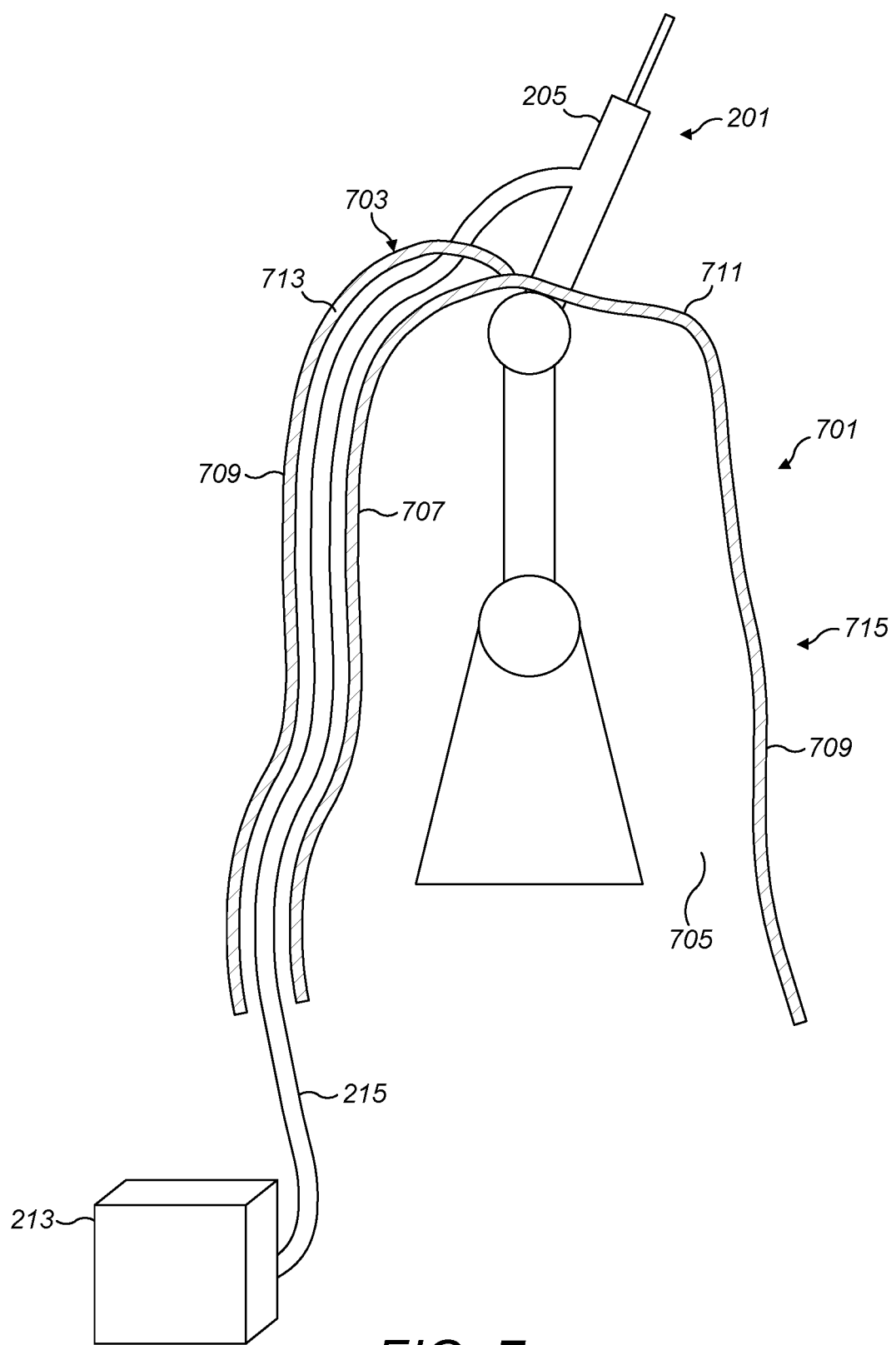
FIG. 7 shows a cross-sectional view of a surgical drape enveloping a robotic arm, where the drape comprises two layers of material in cross-section only in the vicinity of the power cable.

FIG. 7 shows an example of a surgical robot set up to perform a surgical procedure. In this example the surgical robot is the same robot 201 described with reference to FIG. 2. A drape 701 envelopes the robotic arm to define a sterile boundary thereover. The drape is shown in cross-sectional view (indicated by the hatched markings). The drape comprises a sheet 703 that defines a cavity 705 that houses the robotic arm. The sheet comprises an interior surface 707 and an exterior surface 709. The interior surface interfaces with the cavity 705 and the exterior surface interfaces with the external environment.

The surgical instrument 205 is powered by power supply 213. Power is supplied to the instrument from the power supply through power cable 215. The cable is interposed between the interior and exterior surfaces of the sheet.

The drape sheet 703 comprises two layers of material 711 and 713. The drape is configured so that the sheet comprises the two layers of material in cross-section only in regions of the sheet in proximity to, or in the vicinity of the power cable. That is, in regions of the sheet remote from the power cable, such as the region indicated generally at 715, the sheet comprises only a single layer in cross-section. In regions of the sheet in proximity to or in the surrounding area of the cable, the drape sheet comprises two material layers in cross section. In this way the secondary layer can be viewed as forming a pocket for the cable. The drape sheet thus only contains the secondary layer where needed, that is to house the cable. This is advantageous because it may reduce the amount of material required to manufacture the drape sheet.

The drape sheet may comprise a primary material layer (e.g. layer 711) and a secondary material layer (e.g. 713). The primary layer of material may have a larger surface area than the secondary layer of material. The primary and secondary layers may therefore not be congruent. The primary layer may define the inner surface of the drape sheet. The secondary layer may define an outer surface of the drape sheet such that the power cable is interposed between an exterior surface of the secondary layer and an inner surface of the primary layer. The outer surface of the drape sheet may therefore comprise a surface of the primary layer and a surface of the secondary layer.

The secondary layer may comprise an opening, or port to enable the power cable to traverse the outer surface of the drape sheer for connection to the instrument. The primary layer may comprise an opening or port to enable the power cable to traverse the interior surface of the sheet to connect to the power supply. The first and second layers may alternatively define a mouth at the perimeter of the drape through which the power cable can extend.

Figure 5:
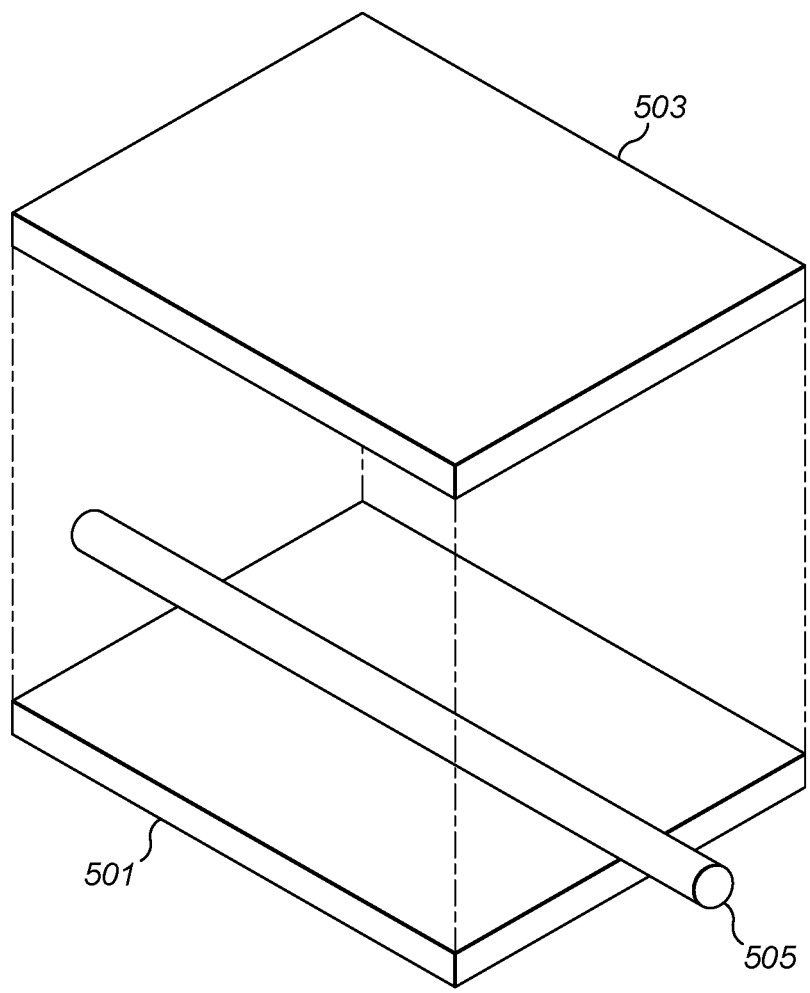
FIG. 5 is an illustration of how a drape may be constructed.

A drape such as drape 701 may be manufactured in a similar manner to the process illustrated in FIG. 5. The process may differ in that, rather than adhering together two congruent sheets as in FIG. 5, a primary layer may be adhered to a secondary layer with a smaller surface area than the primary layer. The primary and secondary layers may be equal in one length dimension but differ in another perpendicular length dimension. E.g. the layers may be of the same length but of differing widths. Alternatively the primary and secondary layers of material may have different lengths along both perpendicular directions, i.e. the primary and secondary layers have different lengths and widths. The secondary layer may for example be formed in a strip that is adhered to the primary layer.

Figure 8:
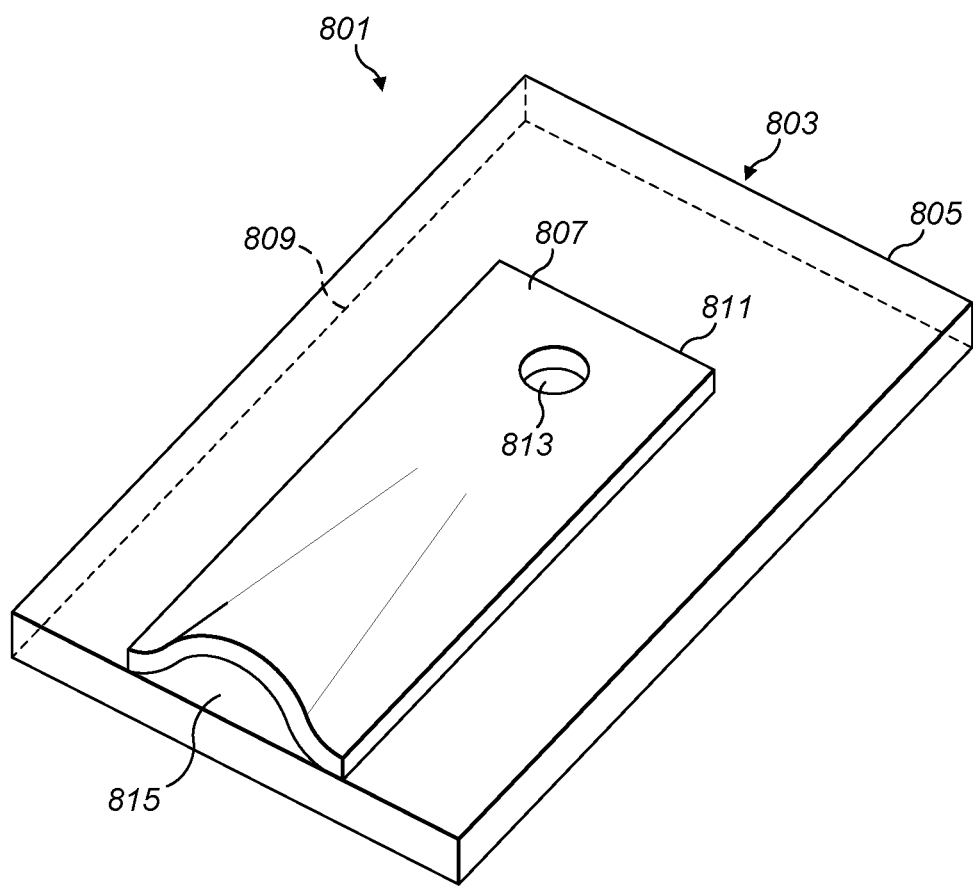
FIG. 8 shows a planar arrangement of an example drape with two layers of material in cross-section only in the vicinity of the power cable.

FIG. 8 shows how the secondary layer can be adhered to the primary layer to form a channel or conduit for the power cable. A drape 801 is shown in a planar arrangement. The drape comprises a sheet 803 that comprises a primary layer of material 805 and a secondary layer of material 807. The secondary layer is formed as a strip, or general elongate shape and has a smaller surface area than the primary layer. The surface area of the secondary layer may be less than 40%, or 20% of the primary layer, for example. The secondary layer is adhered to the primary layer to form a channel or conduit that houses the power cable (not shown).

When the cable is housed within the channel the cable is interposed between an interior surface of the sheet 809 (the interior surface being defined by a surface of the primary layer of material) and an exterior surface of the sheet 811 (the exterior surface being defined by a surface of the secondary layer of material). The secondary layer may comprise an opening or port 813 through which the power cable can extend to traverse the exterior surface of the sheet to connect to the robotic instrument. The channel may have a mouth 815 as shown that is located at the perimeter of the drape. The mouth comprises an opening bounded by a lip formed from material of the primary layer and the secondary layer. The cable can extend out of the mouth to connect to the power supply.

Alternatively, the secondary layer may be adhered along its entire perimeter to the primary layer. In other words there may be no mouth 815. In this case, the power cable traverses the drape sheet to connect to the power supply by passing through a second port or opening located on either the primary layer or the secondary layer.

The above description illustrates various examples of how a supply line (in the form of a power cable) can be integrated within the sheet of a surgical drape by interposing the cable between interior and exterior surfaces of the sheet. A further set of examples will now be described that illustrate a further approach to securing a supply line to the sheet of the drape. In the following examples, the drape comprises a set of routing structures, or elements, that are attached to the sheet. These structures may also be referred to as guiding elements. The drape is configured so that each element can receive a threaded supply line for use in a surgical procedure. That is, the drape is configured so that a supply line can be threaded through each element of the set and thereby be secured to the sheet of the drape. This advantageously allows the supply line to be secured in place during a surgical procedure without having to manually tie the supply line in place using clips, ties etc., which may be difficult and somewhat cumbersome.

Figure 9:
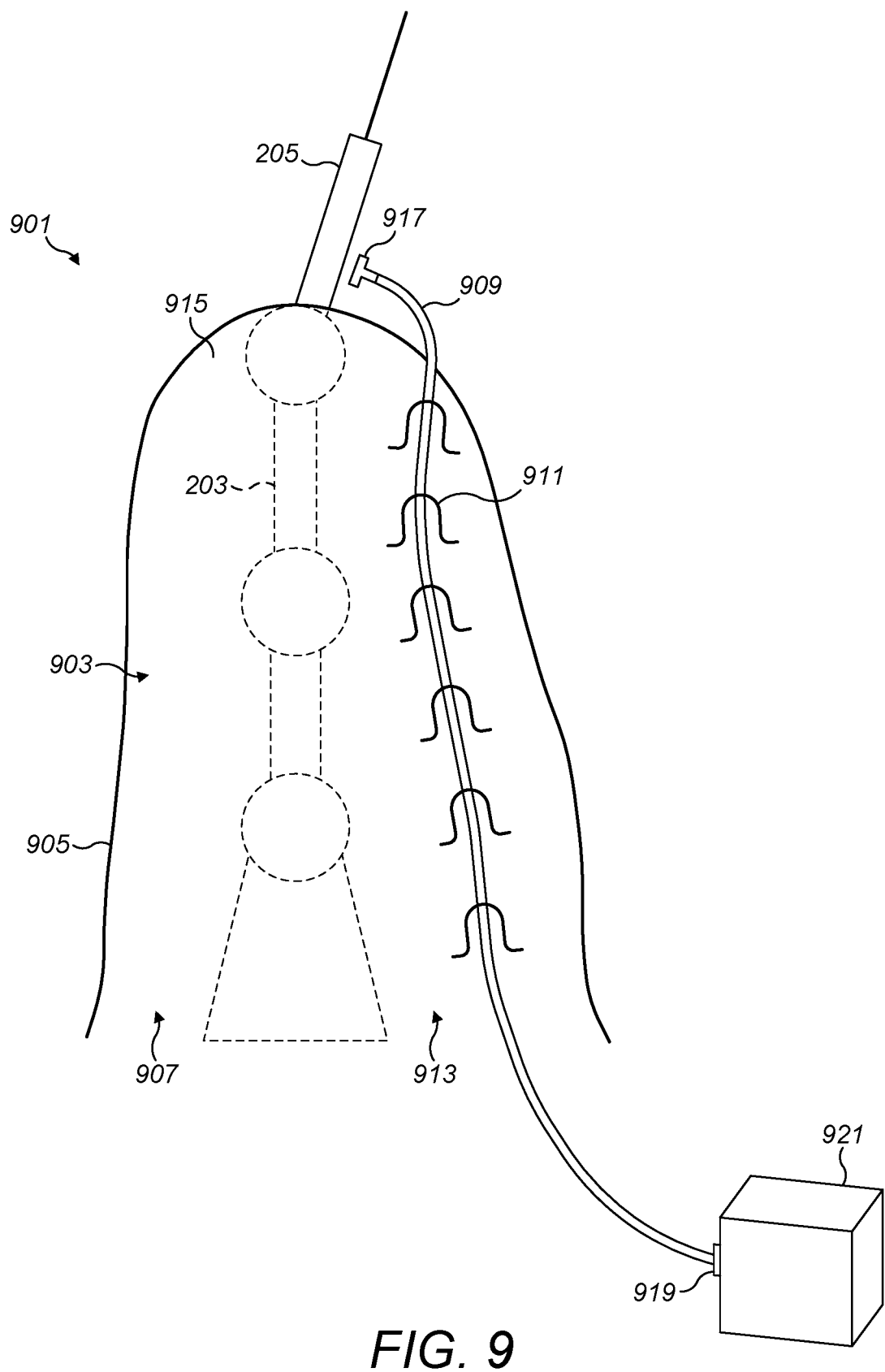
FIG. 9 shows an example of a surgical robotic system comprising a supply line threaded through guiding elements to secure the supply line to the sheet of the drape.

FIG. 9 shows an example of a surgical robotic system set up for a surgical procedure. The robotic system is shown generally at 901 and comprises robotic arm 203 and surgical instrument 205. The instrument 205 is attached to a distal end of the robotic arm. Surgical drape 903 is shown enveloping the robotic arm to define a sterile boundary thereover. As before, the drape comprises a sheet 905 that defines a cavity 907 that houses the robotic arm 203. The sheet may be flexible, as described above. The cavity has a basal portion 913 and a distal portion 915. The basal portion includes the mouth, or opening, of the cavity. The distal portion of the cavity is closed.

A supply line 909 for use in a surgical procedure is shown that in this example attaches to the surgical instrument. The supply line terminates at a first of its ends in an instrument connector 917 for connecting to the surgical instrument. The supply line may terminate in a second of its ends in a supply connector 919 for connecting to a supply source 921. The supply source 921 could for example be an electrical power supply or generator (if the supply line were a power cable) or an irrigation or suction pump if the supply line were an irrigation or suction tube.

The supply line is secured to the sheet via a set of one or more guiding elements 911. The guiding elements are shown attached to the exterior surface of the sheet 905, and retain the supply line in position along the sheet. Here, the supply line is threaded through the set of routing elements so that the routing elements retain the supply line. The routing elements 911 are thus intermittently spaced on the sheet. The routing elements may take various forms: for example, each routing element may be in the form of a loop of material defining an eyelet; alternatively a routing element could be a sleeve of material, where the sleeve defines a lumen through which the supply line is threaded. Some examples of the various different forms of routing element are shown in FIGS. 10A-10D. Each of these examples shows the routing element attached to the sheet 905 (of which only a portion is shown for clarity).

Figure 10A:
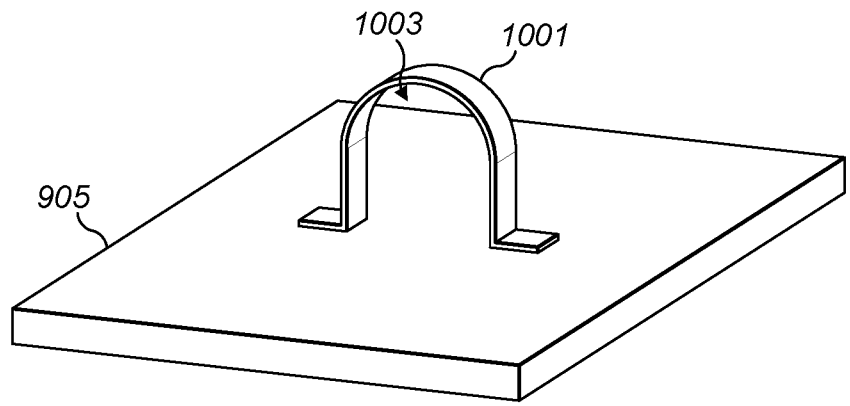
FIGS. 10A-10D show various examples of the guiding elements.

A routing element in the form of a loop is shown in FIG. 10A and denoted at 1001. The loop of material may be secured to the sheet to define an eyelet 1003 for receiving the supply line. The loop of material may be integral with the sheet. It could for example be adhered to the sheet. The loop may be formed from a strip of material secured to the sheet at its lateral ends. The routing element may be made of the same material as the sheet. Alternatively, the material of the routing element may be different from that of the sheet. It may be advantageous to make the routing element of a thicker, or more durable, material than the material of the sheet so that the routing elements can adequately support the supply line during a surgical procedure.

Figure 10B:
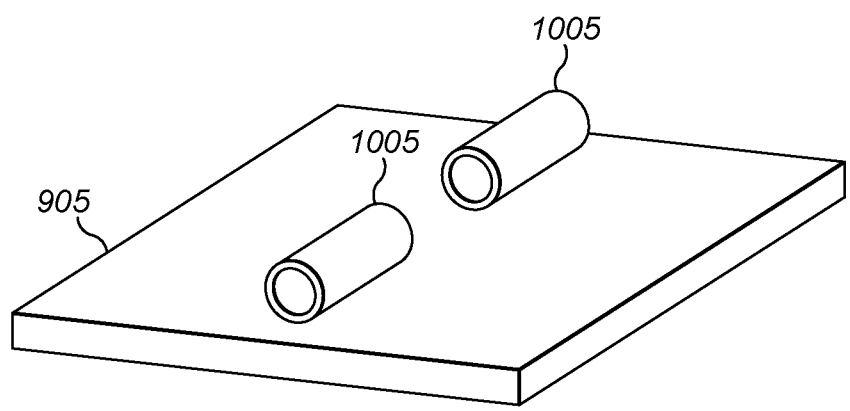

Alternatively the routing elements may take the form of a set of conduit portions, or sleeves, as shown in FIG. 10B. Here, the routing element 1005 is attached to the sheet to define a sleeve, or conduit, through which the supply line is threaded. Again, the set of conduit portions are intermittently spaced on the sheet. The sleeve may be defined entirely by the material of the routing element. This has the advantage of facilitating easy construction of the drape as each sleeve can simply be adhered to the sheet. Alternatively, the sleeve may be defined in part by the material of the routing element and in part by the material of the sheet.

Figure 10C:
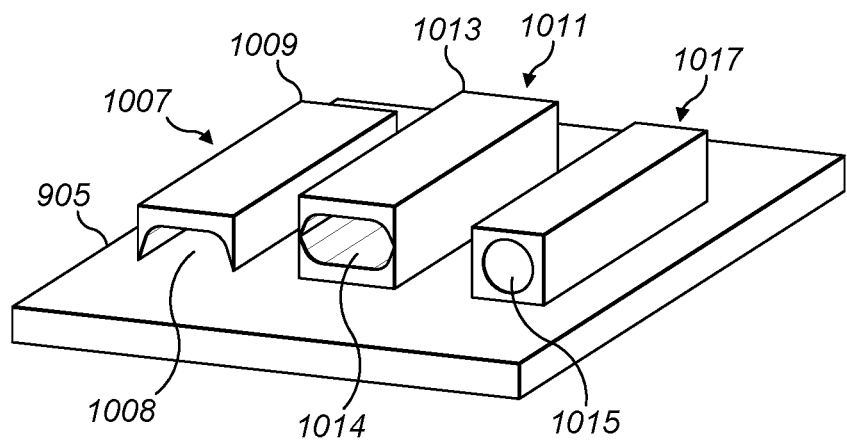

FIG. 10C shows some further examples of the guiding element. In these examples the guiding element is in the form of a housing that defines a channel for receiving the guiding element. Element 1007 is in the form of a housing 1009 having an internal grooved surface 1008 for retaining, or guiding, a supply line. Element 1011 shows a housing 1013 containing two opposing grooved surfaces as shown at 1014. Alternatively, the housing may comprise a bore 1015 as shown for element 1017. In this case the supply line is threaded through the bore 1015. The housing may be a rigid structure (as shown in the examples in FIG. 10C) to facilitate easy attachment to the sheet and/or to enable the supply line to be threaded more easily.

Figure 10D:
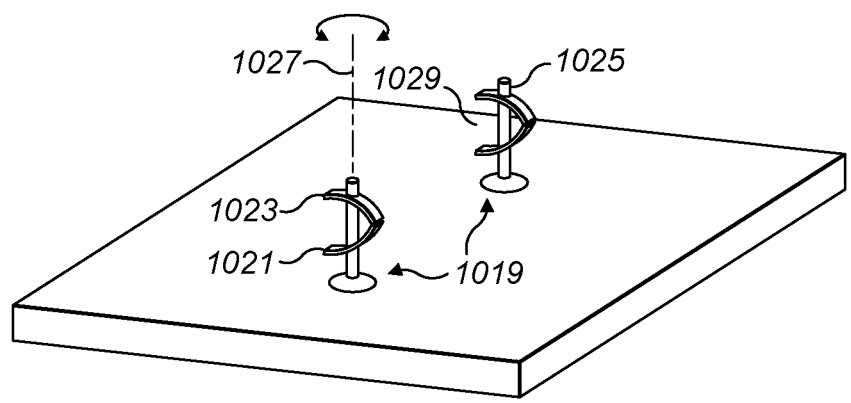

FIG. 10D shows an example in which the guiding element is in the form of a clasp 1019. In this particular example the clasp is adjustable. The clasp comprises two opposing arms 1021 and 1023 where the spacing 1029 between the arms can be adjusted by means of a screw 1025. Of course, other mechanisms for adjusting the clasp are possible. For example, the arms of the clasp may be resiliently deformable so that the spacing between the arms can be increased upon application of a force. The arms may be biased towards a closed position so that the routing element can securely retain the supply line.

Other examples of guiding element are possible. For instance, the guiding element may be a clip into which the supply line can be push-fitted. It may be a peg.

Although the routing elements have been described as possibly being adhered to the sheet, in other examples they may be releasably attached to the sheet so that they may be detached by the user. For example, the routing elements may be attached to the sheet by a fastening mechanism such as a push-fit or snap-fit attachment, a zip-lock mechanism, or a hook and loop fastener (e.g. Velcro). Making the routing elements detachable from the sheet may allow a set of routing elements to be reused following a procedure. The drape sheet may be designed to be disposable, in which case reusable routing elements may reduce the cost of the drape to medical professionals or organisations who perform large numbers of surgical procedures.

During a surgical procedure, articulations of the robotic arm may cause the supply line to coil or bend. Because the supply line is retained by the routing elements, such motion of the supply line may in turn impart large forces through the sheet. The drape sheet 905 may therefore be additionally reinforced in regions surrounding each routing element. The use of a set of reinforcement elements may prevent damage to the sheet (e.g. ripping or tearing) caused by such articulations of the robotic arm during use. For example the drape may comprise a set of patches adhered to the sheet. Each guiding element may be attached to a respective patch. The patches may be made of the same material as the sheet. Alternatively, the patches may be made of a material with a greater resilience and/or shear strength than the material of the sheet. The patches may be flexible to permit an order of compliance so as to not adversely affect the flexibility of the drape. Alternatively the patches may be in the form of rigid plates for increased protection and reinforcement. The patches may be adhered on one side to the sheet 905. On its other side it may be attached to a guiding element. The reinforcement elements may alternatively be flanges each configured to attach to both a guiding element and the drape sheet. The reinforcement element may be attached to the guiding element by any suitable connection, for example it may be adhered to the guiding element, fixed by one or more screws, etc.

In another example, the drape sheet 905 may be reinforced by having regions of increased thickness surrounding the guiding elements. That is, the sheet may have a non-uniform thickness. It may have multiple regions, or subareas, of increased thickness. Each guiding element may be attached to a region of increased thickness. These regions may be spatially arranged across the sheet.

Although the guiding elements 911 retain the supply line, they may not hold it fast. That is, the routing elements may be arranged to permit relative movement of a threaded supply line and the drape sheet 905. The guiding elements may for example permit a degree of lateral and/or longitudinal motion of the supply line (the terms lateral and longitudinal being relative to the general direction of the supply line) relative to the guiding element and/or sheet. As a simple example, each guiding element may encircle, or bound, the supply line but may not circumscribe it. Referring back to FIGS. 10A-D, the eyelet 1003 defined by the loop of material may have a larger cross-sectional area than the supply line; or the sleeve 1005 or bore 1015 may have a larger cross-sectional area and/or diameter than the supply line. Thus, the guiding element may permit slidable motion of the supply line relative to the sheet. The conduit portion of FIG. 10B and the housing of FIG. 10C may be particularly well suited to permit such slidable movement of the supply line.

In another example, the guiding element itself may be moveable relative to the drape sheet 905. The guiding element may for example be rotatable, e.g. about an axis generally perpendicular to the local plane of the sheet (i.e. the general plane of the sheet in the vicinity of the guiding element). Referring back to FIG. 10D, the clasp 1019 may be rotatable about axis 1027 as indicated by the double-headed arrow, for example. The guiding elements shown in FIGS. 10A-10C may also be made rotatable with respect to the sheet, for example by being secured to a support plate, or backing, that is rotatably mounted to the sheet. The guiding element may be fast with a plate that is itself rotatably attached to a backing plate attached to the sheet. In these examples, the rotation of the guiding elements permits movement of the supply line with respect to the sheet and may enable the route adopted by the supply line across the sheet to be altered as the robotic arm is articulated.

Permitting the supply line to move relative to the drape sheet when retained by the guiding elements may prevent the supply line from interfering with the articulations of the robotic arm and/or prevent articulations of the robotic arm from deforming the supply line or altering its configuration in a way that adversely affects its performance. This is because any movement of the robotic arm that imposes a strain on the supply line could simply cause the supply line to move to a position of reduced strain (e.g. by causing the guiding element to rotate or by causing the supply line to coil). Allowing the guiding elements to rotate may be particularly useful for accommodating rotational movement of one or more limbs of the robot arm about roll joints.

To further accommodate movement of the robotic arm 203, the drape may be arranged so that the supply line is slack in regions between adjacent guiding elements, rather than being taut. By arranging the supply line to be slack, it may accommodate greater articulation of the robotic arm.

To prepare the robotic system 901 for a surgical procedure, the supply line may be threaded through the set of guiding elements prior to the drape being fitted over the robotic arm. The drape (including the guiding elements) may then be sterilised. The sterilised drape can then be placed over the robotic arm. The guiding elements may then be suitably positioned for use in the surgical procedure. Securing the supply line to the sheet via the guiding elements may be a more convenient way to retain the supply line in place than having to secure the line with cable ties, tape etc.

Furthermore, it may be seen with reference to FIG. 9 that the set of routing elements may advantageously be positioned on the sheet 905 so that the threaded supply line is suitably positioned for use in the surgical procedure when the drape houses the robotic arm. That is, the routing elements may be positioned on the sheet so that the working end of the supply line (i.e. the end that connects to the robotic instrument 205) is positioned in the vicinity of the surgical site or in the vicinity of the instrument socket that the supply line connects to (e.g., to a power socket located on the instrument in the example that the supply line is a power cable). To suitably position the supply line, the guiding elements may be arranged so as to traverse the longitudinal extent of the cavity defined by the sheet 905. In other words, the set of guiding elements 911 may be disposed on the sheet in a similar manner to that shown in FIG. 9 from the basal portion of the cavity 913 to the distal portion 915. Placing the guiding elements along the longitudinal extent of the cavity means that, when the supply line is threaded through the set of guiding elements, the supply line is routed by the guiding elements along the cavity. The closed end of the cavity is the portion located between the robotic arm 203 and surgical instrument 205, and so placing one or more guiding elements in this region assists with positioning the working end of the supply line for use in the surgical procedure. In another arrangement, the guiding elements may be positioned on the drape so that they extend along the general direction of the robotic arm 203. That is, the guiding elements may follow the contour of the arm, or traverse the length of the arm. Such an arrangement assists with correctly positioning the terminal ends of the supply line for use in the surgical procedure whilst also reducing the chance that the supply line will interfere with the articulations of the arm.

Arranging the guiding elements on the sheet so that they route a threaded supply line towards the instrument when the drape covers the arm can facilitate an easier set-up of the surgical system for a procedure. This is because simply placing the drape over the arm brings the supply line broadly into position for use in the surgical procedure. The person preparing the robotic system for surgery may then simply manoeuvre the terminal end of the supply line to correctly align it for use in the procedure (e.g. by connecting it to the interface on the robotic instrument).

The above examples describe a drape with guiding elements for retaining a single supply line. In other examples there may be multiple supply lines to be retained in position by the guiding elements, for example a power supply for the robotic instrument and an irrigation tube to remove debris and fluid from the surgical site.

One approach to retain multiple supply lines is to configure each guiding element in the set 911 to be able to receive multiple supply lines. That is, the guiding elements may be dimensioned so that multiple supply lines can be threaded through each element of the set. For example, referring back to FIGS. 10A-D, each of the guiding elements 1001, 1005, 1007, 1011, 1017 or 1019 may be dimensioned to receive multiple supply lines. In this regard, the adjustable clasp may be particularly useful since the size of the receiving space 1029 can be readily adjusted in dependence on the number of supply lines (or the thickness of the supply line) to be retained by the guiding elements.

Figure 11:
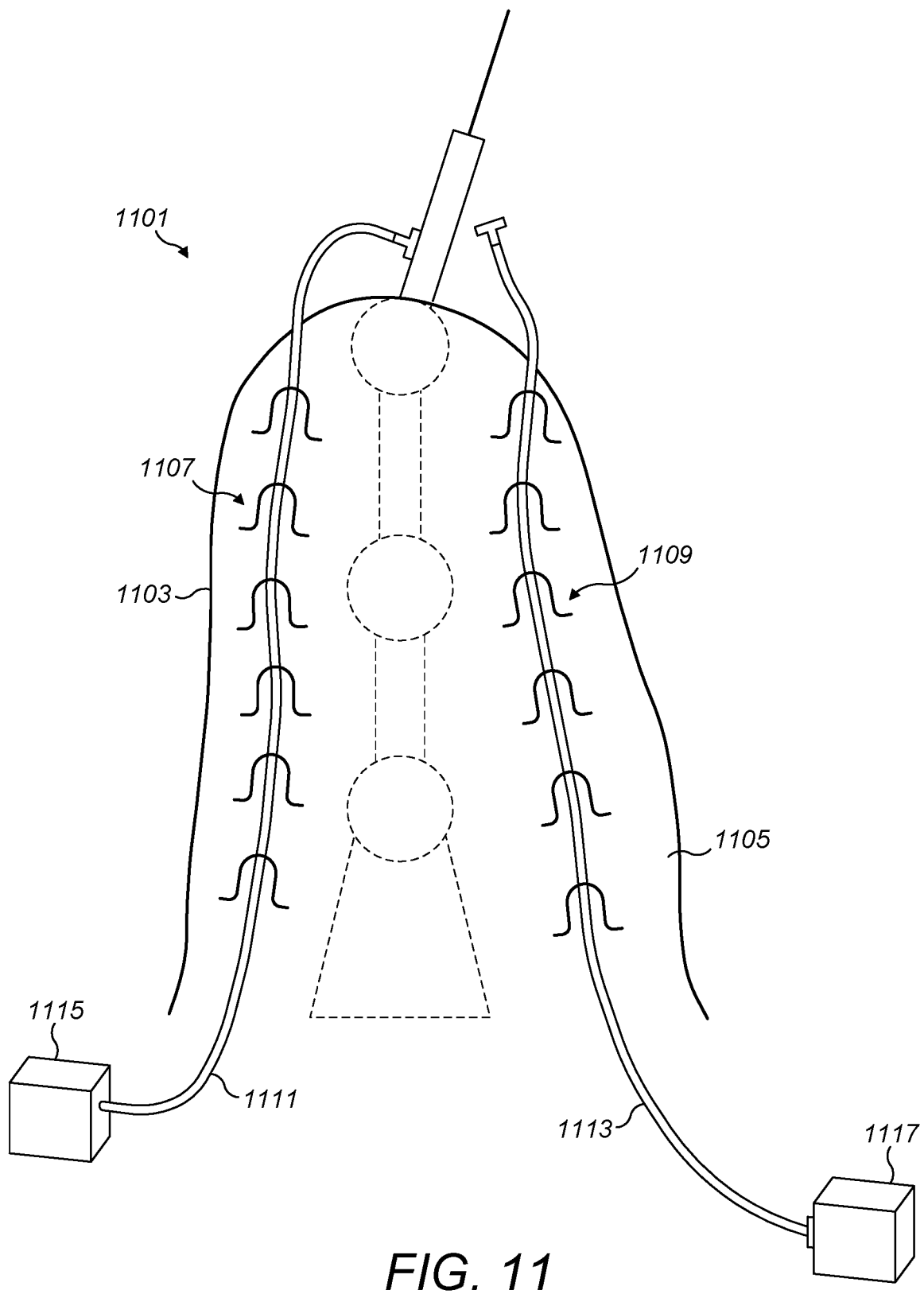
FIG. 11 shows another example of a surgical robotic system comprising two supply lines threaded through respective sets of guiding elements.

An alternative approach to retain multiple supply lines is to provide first and second sets of guiding elements, where each set of guiding elements retains a respective supply line. FIG. 11 shows a robotic system 1101 comprising a drape 1103 that envelopes robotic arm 203. The sheet 1105 of the drape comprises a first set of guiding elements 1107 and a second set of guiding elements 1109 each configured to retain a respective supply line (denoted 1111 and 1113 respectively). Both sets of guiding elements route a supply line along the cavity defined by the sheet towards the instrument 205 for use in a surgical procedure. Supply line 1111 is shown connected to a supply source 1115 (which may for example be a power supply) and supply line 1113 is shown attached to supply source 1117 (which may for example be a suction device for use an irrigation tube). The sheet 1105 may additionally be reinforced in the areas surrounding the guiding elements in the manner described above.

The guiding elements of each set may be any of the types described herein. The guiding elements of the first set may be of the same type or a different type to the guiding elements of the second set. For example, the first set of routing elements may be in the form of an adjustable clasp 1015 and the second set of routing elements may be in the form of conduit portions 1005; routing elements of both sets may be in the form of loops, etc.

Retaining different supply lines in respective sets of routing elements may have the advantage of providing a degree of fault tolerance by providing a degree of spatial separation between the supply lines. Thus, if one of the supply lines suffers damage (e.g. an irrigation tube), another supply line (e.g. the power cable) is less likely to suffer consequential damage from, e.g. leaked fluids, compared to if the supply lines were retained in a single set of guiding elements.

Although the drape shown in FIG. 11 comprises two sets of guiding elements, in a more general example it may comprise N sets of guiding elements for retaining a respective supply line, where N 2. Each of the sets of guiding elements may be of the same type (e.g. a sleeve), or each may be of a different type.

In the examples described above with respect to FIGS. 9 to 11, the guiding elements are attached to the exterior surface of the sheet. It will be appreciated that for each of the above examples the guiding elements may alternatively be attached to the interior surface of the sheet (i.e. the surface of the sheet that interfaces with the non-sterile region within the cavity). This may negate the need to have to sterilise the supply line in order to prepare the drape for surgical use because the supply line would no longer be interfacing directly with the sterile environment.

If the guiding elements are attached to the inside surface of the sheet, the drape may further comprise an opening through which the supply line passes. This is so that the terminal end of the supply line is on the exterior-side of the sheet (i.e. external of the cavity), so that the supply line is suitably positioned for use in the surgical procedure. The opening may as such be located at or towards the distal end of the cavity. In order to maintain the sterile boundary, the opening may be sealed against the supply line. The seal may be air-tight.

The examples described above with reference to FIGS. 9 to 11 illustrate how a supply line can be retained in position by being threaded through a set of guiding elements attached to the surgical sheet of the drape. The use of the guiding elements may facilitate easier set-up of the robot for a surgical procedure. The step of securing the supply line(s) to the drape sheet may be performed by the user. That is, the drape and the supply line may be separate components that the user assembles for use in a surgical procedure. For example, the user may select the supply line they wish to attach to the drape (e.g. an instrument power cable), secure the supply line to the drape by the set of guiding elements, sterilise the drape (including the supply line) and then place the sterilised assembled drape over the robotic arm for use in the procedure. Alternatively, the drape and supply line may be pre-assembled. That is, the drape may be distributed and sold with the supply line already assembled. This may further expedite set-up of the surgical robot by removing the step of the user threading the supply line through the guiding elements or otherwise securing the supply line to the drape via the guiding elements. The drape may be assembled with a variety of different supply lines. It may be assembled with more than one supply line threaded through a single set of guiding elements. If the drape comprises multiple sets of the guiding elements for retaining respective supply lines, then the drape may be pre-assembled so that only one supply line (e.g. a power cable) is pre-installed into the drape. Other supply lines (e.g. an irrigation tube) could then be added by the user prior to use. More generally, if the drape comprises N sets of guiding elements, the drape may be pre-assembled with n (where n<N) supply lines. This may provide the benefit of expedited assembly of the robotic system whilst also providing a degree of flexibility in allowing the user to add further supply lines as they require.

Above there have been described different examples of how a supply line can be integrated with a sheet of a surgical drape. The supply line is used in a surgical procedure, e.g. to service the surgical instrument or to maintain a surgical site. As has been mentioned, the supply line could be a power cable for supplying power to a surgical instrument. The power cable itself may comprise a conductive core to supply current generated by the power supply to the robotic arm instrument. The conductive core may be surrounded by an insulating sheath. The insulating sheath may function to prevent current leakage from the conductive core. It may additionally serve as a safety feature to prevent a user from coming into electrical contact with the cable. The insulating sheath may be an intrinsic part of the power cable. That is, the power cable may comprise the conductive core and the insulating sheath. Alternatively the cable may consist of a conductive core (that terminates at each of its ends in a connector), with the insulating sheath being provided by the drape sheet when the cable is integrated therewith.

The conductive core may take many different forms. For example, the conductive core may be a solid core. A solid core is a single-strand wire, or conductive strip, typically formed from a single piece of conductive material. A solid-core is typically one of the cheaper and simpler cores to manufacture. Alternatively the conductive core may comprise a plurality of conductive strands. Such a core may be referred to as a stranded core. The strands may be in a parallel arrangement, or in a braided or twisted arrangement. Stranded core cables may offer greater compliance and flexibility compared to solid core cables, which may make them particularly suitable for use in the surgical drape.

The power cable may comprise a plurality of conductive cores. Such a cable may be referred to as a multicore cable. Each core of the multicore cable may be a solid core, or a stranded core. The plurality of cores may be held together by a single outer sheath.

The insulating sheath may be formed from the material of the drape sheet. For example, the power cable integrated with the drape may not have an intrinsic, or constituent, insulating layer; it may just comprise the conductive core. When the cable is interposed between the interior and exterior surfaces of the drape sheet, the conductive core interfaces directly with material of the sheet, the sheet thereby functioning as the insulating layer for the cable.

A power cable that does not have an intrinsic insulating layer/sheath may be used with any of the example drapes described with reference to FIGS. 1 to 8. Using just a conductive core for the power cable may result in a drape with greater flexibility compared to using a power cable that comprises an insulating layer. It may also reduce the cost of manufacturing the drape because no separate insulator for the cable is required.

The power cable may alternatively comprise an insulating layer/sheath for covering the conducting core. This insulating layer is intrinsic to the cable and separate from the material of the sheet. That is, the power cable comprises its own insulating sheath that is not integral with the material of the drape sheet. Such a cable may be used with any of the examples described herein. Such a cable could be a coaxial cable, for example. In the event the cable is a multicore cable, each of the plurality of cores may be covered by a respective insulating sheath. The plurality of cores may be covered by a single protective sheath to maintain the cores in a bundled arrangement. Power cables that comprise an insulating sheath may be more widespread than cables without a sheath, which may make the manufacturing process of the drape more versatile.

Of course, the supply line may not be a power cable but could for example be an irrigation tube, a suction tube, a data-communication line etc.

In some examples described herein, the supply line traverses the exterior surface of the drape to connect to a surgical instrument. In alternative embodiments, the supply line (e.g. power cable) may connect to the surgical instrument through the drape sheet. For example, the drape may comprise an interface plate that is configured to connect to both the surgical instrument and the power cable. The interface plate may be embedded within the sheet. It may be positioned towards the distal end of the cavity so as to be in proximity to the surgical instrument during use of the drape. The plate may comprise one or more conductive contacts that permit the power cable to electrically couple to the instrument. The power cable may be integral with the interface plate. For example the power cable may be adhered to, or fused to, the plate. As such the power cable may be in permanent electrical contact with the plate. In such a drape, the power cable may be connected to the surgical instrument by appropriately positioning the drape relative to the instrument so that the electrical contact of the plate interfaces or connects to a conductive element on the instrument. The conductive contacts of the interface plate may be moulded into an appropriate shape for connection to the surgical instrument. For example the contacts may be in the form of projections that mate with an electrical contact on the instrument.

By having the cable connect to the instrument through the drape, the cable including the instrument connector can be embedded within the sheet and need not traverse the exterior sheet of the drape. This is advantageous because it enables the power cable to connect to the surgical instrument without requiring the power cable to enter the sterile environment.

In some of the examples described herein, a surgical drape has an embedded/integral or, more generally, a secured power cable for supplying power to a surgical instrument attached to a surgical robotic arm. The power cable may be configured to supply power to an instrument used to perform electrosurgery, or electrocautery. Electrosurgery and electrocautery are based on the general principle of using an electrical current to perform surgical procedures on a patient's tissue, for example to cut, coagulate, desiccate or fulgurate the tissue. In general, electrocautery uses a DC current to heat a surgical probe to a high temperature. The heated probe is then applied to the patient's tissue. In contrast, electrosurgery in general applies an AC current directly through the patient's tissue via a pair of electrodes. The frequency of the AC current is typically in the radio frequency (RF) range (e.g. around 500 KHz), and so instruments used for electrosurgery may need to be connected to an RF power supply (for example generator 213). The power cable may therefore be configured to supply RF power to the surgical instrument. The instrument used in electrosurgery may be a monopolar instrument or a bipolar instrument. A monopolar instrument refers to an instrument that comprises one relatively small 'active' electrode placed locally to the surgical site that concentrates the applied current, and one relatively large 'dispersive' electrode placed remotely from the surgical site (but still attached to the patient). The relatively large electrode is used to include a substantial part of the patient's body as part of the electrical circuit. In contrast, a bipolar instrument comprises only two 'active' electrodes so that only the tissue positioned between the two electrodes forms part of the electrical circuit. It will be appreciated that the power cable may be used to supply power to other types of surgical instrument and/or to instruments used in performing other types of surgical procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A drape comprising:
 a sheet, the sheet comprising an interior surface and an exterior surface, the interior surface being configured to define a cavity to envelop a portion of a robotic arm, wherein the interior surface interfaces with the cavity and the exterior surface interfaces with an environment external to the cavity, the interior surface and the exterior surface defining a conduit between the interior surface and an innermost portion of the exterior surface of the sheet, the interior surface separating the conduit from the cavity, the exterior surface defining a port; and a supply line located within the conduit, the supply line comprising a conductive core surrounded by the conduit, wherein the sheet directly contacts the conductive core and the interior surface is located between the cavity and the supply line, the supply line configured to extend through the port from the conduit to the environment external to the cavity.

2. The drape as claimed in claim 1, wherein the supply line terminates at a first of its ends in an instrument connector configured to connect to a robotic-arm instrument.

3. The drape as claimed in claim 2, wherein the supply line is a power cable for supplying power to the robotic-arm instrument.

4. The drape as claimed in claim 3, wherein the power cable comprises a first terminal end for connecting to a power supply and a second terminal end for connecting to the robotic-arm instrument.

5. The drape as claimed in claim 2, wherein the supply line traverses the exterior surface of the sheet proximal to the instrument connector.

6. The drape as claimed in claim 1, wherein the drape is for enveloping the portion of the robotic arm and wherein the supply line is for use in a surgical procedure.

7. The drape as claimed in claim 1, wherein the supply line is sandwiched between the interior and exterior surfaces of the sheet.

8. The drape as claimed in claim 1, wherein the supply line is housed within the conduit defined by the sheet, the conduit terminating at a mouth at least partially defined by at least one of the interior surface or the exterior surface, the mouth located at a perimeter of the drape.

9. The drape as claimed in claim 1, wherein the cavity is an elongate cavity and the drape is arranged so that the supply line extends along a longitudinal extent of the cavity and extends between an opening mouth of the cavity for housing a basal portion of the robotic arm and a distal end of the cavity for housing a distal portion of the robotic arm.

10. The drape as claimed in claim 1, wherein the drape is a surgical drape.

11. The drape as claimed in claim 1, wherein the sheet comprises the interior surface and the exterior surface only in proximity of the supply line.

12. A drape comprising:
an interior sheet and an exterior sheet,
wherein:
the interior sheet is configured to define a first cavity to envelop a portion of a robotic arm;
the exterior sheet is configured to define a second cavity which includes and extends beyond the first cavity;
the interior sheet interfaces with the first cavity; and
the exterior sheet defines a port and interfaces with an environment external to the second cavity; and
the interior and exterior sheets define a conduit between the interior sheet and an innermost portion of the exterior sheet, the interior sheet separating the conduit from the first cavity; and a supply line located in the conduit, the supply line comprising a conductive core surrounded by the conduit, wherein the conduit directly contacts the conductive core and the interior sheet is located between the first cavity and the supply line, the supply line configured to extend through the port from the conduit to the environment external to the second cavity.

* * * * *